(12) United States Patent
Latino et al.

(10) Patent No.: US 7,736,494 B2
(45) Date of Patent: Jun. 15, 2010

(54) OZONE DELIVERY SYSTEM INCLUDING A VARIABLE PITCH GAS-FLUID CONTACT DEVICE

(75) Inventors: Joseph S. Latino, Brooklyn, NY (US); Steven A. Keyser, Salt Lake City, UT (US)

(73) Assignee: AcquiSci, Inc., Belmar, NJ (US)

( * ) Notice: Subject to any disclaimer, the term of this patent is extended or adjusted under 35 U.S.C. 154(b) by 819 days.

(21) Appl. No.: 10/963,477

(22) Filed: Oct. 11, 2004

(65) Prior Publication Data

US 2005/0051498 A1    Mar. 10, 2005

Related U.S. Application Data

(63) Continuation-in-part of application No. 10/910,485, filed on Aug. 2, 2004, now abandoned, and a continuation-in-part of application No. 10/910,439, filed on Aug. 2, 2004, now abandoned.

(60) Provisional application No. 60/553,774, filed on Mar. 17, 2004, provisional application No. 60/491,997, filed on Jul. 31, 2003.

(51) Int. Cl.
 *C02F 1/78* (2006.01)
(52) U.S. Cl. ............... 210/85; 210/192; 210/205; 210/249; 210/416.1; 422/45; 422/119; 422/186.07; 422/181; 422/193; 261/112.1; 261/DIG. 42

(58) Field of Classification Search .......... 210/85, 210/192, 194, 195.1, 205, 249, 255, 258, 210/760, 416.1; 261/36.1, 112.1, 112.2, 261/DIG. 42; 604/6.14, 25; 422/28, 29, 422/45, 46, 191, 193, 119, 186.07
See application file for complete search history.

(56) References Cited

U.S. PATENT DOCUMENTS 2,865,617 A * 12/1958 Dickens et al. ............ 261/130

(Continued)

FOREIGN PATENT DOCUMENTS

| CA | 1269935 | 4/1986 |
| WO | WO 96/17635 | 6/1996 |

OTHER PUBLICATIONS

Alter, Harvey J, MD, "G-pers creepers, where'd you get those papers? A reassessment of the literature on the hepatitis G virus," Transfusion, vol. 37, pp. 569-572 (Jun. 1997).

(Continued)

*Primary Examiner*—Matthew O Savage
(74) *Attorney, Agent, or Firm*—Morriss O'Bryant Compagni (57) ABSTRACT

An ozone delivery system for delivering and manufacturing a measured amount of an ozone/oxygen admixture, which is able to measure, control, report and differentiate between delivered-ozone and absorbed-dose of ozone. Improved gas-fluid contacting devices that maximize gas-fluid mass transfer may be included. All gas contacting surfaces of the system, including one or more gas-fluid contacting devices are made from ozone-inert construction materials that generally do not absorb ozone or introduce amounts of contaminants or deleterious byproducts of oxidation into a fluid or non-fluid target from ozone oxidation.

7 Claims, 6 Drawing Sheets

U.S. PATENT DOCUMENTS

| | | | |
|---|---|---|---|
| 4,632,980 A | | 12/1986 | Zee et al. |
| 5,052,382 A | * | 10/1991 | Wainwright ........... 128/202.25 |
| 5,126,376 A | | 6/1992 | Herman |
| 5,185,371 A | | 2/1993 | Rubinstein |
| 5,190,977 A | | 3/1993 | Herman |
| 5,211,912 A | | 5/1993 | Rubinstein |
| 5,260,342 A | | 11/1993 | Herman |
| 5,270,344 A | | 12/1993 | Herman |
| 5,281,392 A | | 1/1994 | Rubinstein |
| 5,364,879 A | | 11/1994 | Herman |
| 5,540,898 A | | 7/1996 | Davidson |
| 5,591,457 A | | 1/1997 | Bolton |
| 5,834,030 A | | 11/1998 | Bolton |
| 5,882,591 A | | 3/1999 | Kekez |
| 6,027,688 A | | 2/2000 | Wainwright |
| 6,060,020 A | * | 5/2000 | Piuk et al. ..................... 422/33 |
| 6,204,058 B1 | | 3/2001 | Bolton |
| 6,303,152 B1 | | 10/2001 | Kief |
| 6,399,664 B2 | | 6/2002 | Smith |
| 6,569,467 B1 | | 5/2003 | Bolton |
| 2003/0118473 A1 | | 6/2003 | Sunnen |

OTHER PUBLICATIONS

Bailey, P., et al., "Complexes and Radicals Produced During Ozonation of Olefins", Ozone Reactions with Organic Compounds, pp. 1-8 (May 1971).

Begin, M.E., et al., Selective Killing of Human Cancer Cells by Polyunsaturated Fatty Acids, Prostaglandins Leukotrienes and Medicine, 19:177-86 (1985).

Begin, M.E., et al., Selected Fatty Acids as Possible Itermediates for Selective Cytotoxic Activity of Anticancer Agents Involving Oxygen Radicals, Anticancer Research, 6:291-96 (1985).

Begin, M.E., et al.,Polyunsaturated Fatty Acid-Induced Cytotoxicity Against Tumor Cells and its Relationship to Lipid Peroxidation, J. Nat'l. Cancer Inst., vol. 80, No. 3, pp. 188-194 (Apr. 1988).

Bird, R.P., et al., Comparative Studies on Different Methods of Malonaldehyde Determination, Methods in Enzymology, vol. 105, pp. 299-305 (1984).

Bird, R.P., et al., Determination of Malonaldehyde in Biological materials by High Pressure Liquid Chromatography, Analytical Biochemistry, 128: 240-44 (1983).

Blajchman, M., et al., Bacteria in the Blood Supply: An Overlooked Issue in Transfusion Medicine, Blood Safety: Current Challenges, S.J. Nance ed., pp. 213-28 (1992).

Bocci, V., et al., Studies of the Biological Effects of Ozone 1. Induction of Interferon γ on Human Leucocytes, Haematologica vol. 75, pp. 510-515 (1990).

Bocci, V., et al., Studies on the Biological Effects of Ozone: 2. Induction of Tumor Necrosis Factor (TNF-α) on Human Leucocytes, Lymphokine & Cytokine, vol. 10, No. 5, pp. 409-412 (1991).

Bocci, V., et al., Studies of the Biological Effects of Ozone 3, An Attempt to Define Conditions for Optimal Induction of Cytokines, Lymphokine & Cytokine Research, vol. 12, No. 2, pp. 121-126 (1993).

Bocci, V., et al., Studies of the Biological Effects of Ozone 4, Cytokine Production and Glutathione Levels in Human Erythrocytes, J. Biological Regulators and Homeostatic Agents, vol. 7, No. 4, pp. 133-138 (1993).

Bocci, V., et al., A Reasonable Approach for the Treatment of HIV Infection in the Early Phase with Ozonetherapy (Autohaemotherapy), How 'Inflammatory' Cytokines May Have a Therapeutic Role, Mediators of Inflammation, vol. 3, pp. 315-321, 1994.

Bocci, V., et al., Studies on the Biological Effects of Ozone 7, Generation of Reactive Oxygen Species (ROS) After Exposure of Human Blood to Ozone, Journal Biological Regulators and Homeostatic Agents, vol. 12, No. 3, pp. 67-75 (1998).

Bocci, V., et al., Studies on the Biological Effects of Ozone 8, Effects on the Total Antioxidant Status and on Interleukin-8 Production, Mediators of Inflammation, vol. 7, pp. 313-317 (1998).

Bocci, V., et al., Studies on the Biological Effects of Ozone 9, Effects of Ozone on Human Platelets, Platelet, vol. 10, pp. 110-116 (1999).

Bocci, V., et al., Studies on the Biological Effects of Ozone 10, Release of Factors from Ozonated Human Platelets, Mediators of Inflammation, vol. 8, pp. 205-209 (1999).

Bolton, et al., The Biological Effects of Ozone on Reprsentative Memb ers of Five Groups of Animal Viruses, Environmental Research, vol. 27, pp. 476-484 (1982).

Bowden, R., Cytomegalovirus: Transmission by Blood Components and Measures of Prevention, Blood Safety: Current Challenges, S.J. Nance ed., pp. 201-211 (1992).

Carpendale, M.T.F., et al., Ozone Inactivates HIV at Noncytotoxic Concentrations, Antiviral Research, vol. 16, 1919, pp. 281-292 (1991).

Carrasco, L. The Inhibition of Cell Functions After Viral Infection, FEBS Letters, vol. 76 No. 1, pp. 11-15, (1977).

Carrasco, L., Selective Inhibition of Translation in Transformed Cells FEBS Letters, vol. 110, No. 2, pp. 341-343, (1980).

Chiu, E.K.W., et al., A Prospective Study of Symptomatic Baceteremia Following Platelet Transfusions and of its Management, Transfusion, vol. 34, No. 11, pp. 950-954 (1994).

Corongiu, F.B., et al., An Improved and Simple Method for Determining Diene Conjugation in Autoxidized Polyunsaturated Fatty Acids, Chem.-Biol. Interactions, vol. 44, pp. 289-297 (1983).

Criegee, R., et al., Fragmentation of Ozonides by Solvents, Ozone Reactions with Organic Compounds, Advances in Chemistry, Series 112, pp. 23-24 (1972).

Cross, C.E. et al., FEBS Letters, vol. 298, No. 2, 3, pp. 269-272 (1992).

Cruse and Lewis, Illustrated Dictionary of Immunology, 1995, pp. 168-172.

Dodd, R., Adverse Consequences of Blood Transfusion: Quantitative Risk Estimates, Blood Supply: Rises, Perceptions and Prospects for the Future, S.J. Nance, ed., p. 1-24 (1994).

Easterbauer, H., et al., Chemistry and Biochemistry of 4-Hydroxynonenal, Malonaldehyde and Related Aldehydes; Free Radical Biology & Medicine, vol. 11, pp. 81-128 (1991).

Fletcher, B.L., et al., Measurement of Fluorescent Lipid Peroxidation Products in Biological Systems and Tissues, Analytical Biochemistry, vol. 52, pp. 1-9 (1973).

Garber, G.E., et al., The Use of Ozone-Treated Blood in the Therapy of HIV Infection and Immune Disease: A Pilot Study of Safety and Efficacy, AIDS, vol. 5, pp. 981-984 (1991).

Gregory, S.H., et al., The Role of Colony-Stimulating Factors in Host Defenses, Society for Experimental Biology and Medicine, pp. 349-360 (1991).

Hicks, M., et al., A Spectrophotometric Method for the Determination of Lipid Hydroxyperoxides, Analytical Biochemistry 99, pp. 249-253 (1979).

Hudlickey, T., McGraw-Hill Encyclopedia of Chemistry, Fifth Edition, 1982, pp. 1034-1038.

Lackritz, E.M., et al., Estimated Risk of Transmission of the Human Immunodeficiency Virus by Screened Blood in the United States, The New England Journal of Medicine, vol. 333, No. 26, pp. 1721-1725, (1995).

Larini, A., et al., The Ozone Tolerance: I) Enhancement of Antioxidant Enzymes is Ozone Dose-dependent in Jurkat Cells, Free Radical Research, vol. 37, No. 11, pp. 1163-1168 (Nov. 2003).

Larini, A., et al., Effect of 4-hydroxynonenal on Antioxidant Capacity and Apoptosis Induction in Jurkat T Cells, Free Radical Research, vol. 38, No. 5, pp. 509-516 (May 2004).

Morrow, J. et al., Septic Reactions to Platelet Transfusion: A Persistent Problem, JAMA, vol. 266, No., pp. 555-558 (1991).

Ogawa, M., Differentiation and Proliferation of Hematopoietic Stem Cells, Blood, vol. 81, No. 11, pp. 2844-2853 (1993).

Oxford Biomedical Research, Colorimetric Assay for Lipid Peroxidation, Product No. FR 12, revised Sep. 2003.

Pryor, W.A., et al., Chemical Methods for the Detection of Lipid Hydroxyperoxides, Methods in Enzymology, vol. 105, pp. 293-299 (1984).

Sinnhuber, R.O., et al., Characterization of the Red Pigment Formed in The 2-Thiobarbituric Acid Determination of Oxidative Rancidity, Food Research, Food Research, vol. 23, pp. 626-633 (1958).

Slater, T.F.. Overview of Methods Used for Detecting Lipid Peroxidation, Methods in Enzymology, vol. 105, pp. 283-293 (1984).

Sweet, F., et al., Ozone Selectively Inhibits Growth of Human Cancer Cells, Science, vol. 209, No. 22, pp. 931-933 (1980).

Wells, K.H., et al., Inactivation of Human Immunodeficiency Virus Type 1 by Ozone In Vitro, Blood, vol. 78, No. 7, pp. 1882-1890 (1991).

Yagi, K.: A Simple Fluorometric Assay for Lipoperoxide in Blood Plasma, Biochemical Medicine, vol. 15, pp. 212-216 (1976).

Zanker, K.S., et al., In vitro Synergistic Activity of 5-Fluorouracil with Low-Dose Ozone Against a Chemoresistant Tumor Cell Line and Fresh Human Tumor Cells, Chemotherapy, vol. 36, pp. 147-154 (1990).

* cited by examiner

OZONE DELIVERY SYSTEM INCLUDING A VARIABLE PITCH GAS-FLUID CONTACT DEVICE

CROSS-REFERENCE TO RELATED APPLICATIONS

This application is a continuation-in-part of U.S. application Ser. No. 10/910,485, filed Aug. 2, 2004, now abandoned and also a continuation-in-part of U.S. application Ser. No. 10/910,439, filed Aug. 2, 2004, now abandoned both of which claim the benefit of earlier-filed U.S. provisional application Ser. No. 60/553,774, filed Mar. 17, 2004, and U.S. provisional application Ser. No. 60/491,997, filed Jul. 31, 2003. The disclosures of the foregoing applications are incorporated herein in their entirety.

BACKGROUND OF THE INVENTION

Historically, ozone has been used as a disinfectant or sterilizing agent in a variety of applications. These include fluid-based technologies such as: purification of potable water, sterilization of fluids in the semi-conductor industry, disinfection of wastewater and sewage, and inactivation of pathogens in biological fluids. Ozone has also been used in the past as a topical medicinal treatment, as a systemic therapeutic and as a treatment of various fluids that were subsequently used to treat a variety of diseases.

Previous technologies were incapable of measuring and differentiating between the amount of ozone that was delivered and the amount of ozone actually absorbed and utilized. This meant previous medicinal technologies for use in patients were incapable of measuring, reporting or differentiating the amount of ozone delivered from the amount that was actually absorbed and utilized. This problem made regulatory approval as a therapeutic unlikely. Previous fluid treatment technologies were also incapable of measuring, reporting or differentiating the amount of ozone delivered from the amount that was actually absorbed by a fluid.

In addition, early approaches of mixing ozone with fluids employed gas-fluid contacting devices that were engineered with poor mass transfer efficiency of gas to fluids. Later, more efficient gas-fluid contacting devices were developed, but these devices used construction materials that were not ozone inert and therefore, reacted with and absorbed ozone. This resulted in absorption of ozone by the construction materials making it impossible to determine the amount of ozone delivered to and absorbed by the fluid. Furthermore, ozone absorption by construction materials likely caused oxidation and the subsequent release of contaminants or deleterious byproducts of oxidation into the fluid.

SUMMARY OF THE INVENTION

An ozone delivery system for delivering and manufacturing a measured amount of an ozone/oxygen admixture, which is able to measure, control, report and differentiate between delivered-ozone and absorbed-dose of ozone, is disclosed. Improved gas-fluid contacting devices that maximize gas-fluid mass transfer may be included. All gas contacting surfaces of the system, including one or more gas-fluid contacting devices are made from ozone-inert construction materials that generally do not absorb ozone or introduce amounts of contaminants or deleterious byproducts of oxidation into a fluid or non-fluid target from ozone oxidation.

BRIEF DESCRIPTION OF THE DRAWINGS

To further clarify the above, a more particular description of an ozone delivery system will be rendered by reference to specific embodiments thereof that are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Definitions

An ozone/oxygen admixture refers to a concentration of ozone in an oxygen carrier gas. Various units of concentration utilized by those skilled in the art include: micrograms of ozone per milliliter of oxygen, parts (ozone) per million (oxygen) by weight ('ppm') and parts per million by volume ('ppmv'). As a unit of concentration for ozone in oxygen, ppmv is defined as the molar ratio between ozone and oxygen. One ppmv ozone is equal to 0.00214 micrograms of ozone per milliliter of oxygen. Additionally, one ppm ozone equals 0.00143 micrograms of ozone per milliliter of oxygen. In terms of percentage ozone by weight, 1% ozone equals 14.3 micrograms of ozone per milliliter of oxygen. All units of concentration and their equivalents are calculated at standard temperature and pressure (i.e. 25° C. at 1 atmosphere).

Delivered-ozone is the amount of ozone contained within a volume of an ozone/oxygen admixture that is delivered to a fluid or non-fluid target.

Absorbed-dose of ozone is the amount of delivered-ozone that is actually absorbed and utilized by a measured amount of fluid or a non-fluid target.

Residual-ozone is the amount of delivered-ozone that is not absorbed such that:

Residual-ozone=delivered-ozone−absorbed-dose of ozone.

An interface is defined as the contact between a fluid or non-fluid target and an ozone/oxygen admixture.

Interface-time is the time that a fluid resides within a gas-fluid contacting device and is interfaced with an ozone/oxygen admixture or the time that an ozone/oxygen admixture is in contact with a non-fluid target.

Interface surface area is defined as the dimensions of the surface within a gas-fluid contacting device over which a fluid flows and contacts an ozone/oxygen admixture. For a non-fluid target, it is the surface area of the target to be contacted by the admixture.

Elapsed-time is the time that a fluid circulates through an ozone delivery system, including passage through one or more gas-fluid contacting devices, connecting tubing and an optional reservoir. Interface-time and elapsed-time are equivalent for a non-fluid target.

Ozone-inert materials are defined as construction materials that do not react with ozone in a manner that introduces contaminants or deleterious byproducts of oxidation of the construction materials into a fluid or non-fluid target.

Non-reactive is defined as not readily interacting with other elements or compounds to form new chemical compounds.

Measured-data is defined as information collected from various measuring components (for example, inlet ozone concentration monitor, exit ozone concentration monitor, gas flow meter, fluid pump, data acquisition device, humidity sensor, temperature sensor, pressure sensor, absorbed oxygen sensor) throughout the system.

Calculated-data is defined as the mathematical treatment of measured-data by the data acquisition device.

Ozone Delivery System

An ozone delivery system delivers a measured amount of an ozone/oxygen admixture and is able to measure, control, report and differentiate between the delivered-ozone and absorbed-dose of ozone. The system provides a controllable, measurable, accurate and reproducible amount of ozone that is delivered to a controllable, measurable, accurate and reproducible amount of fluid and controls the rate of ozone absorption by the target resulting in a quantifiable absorbed-dose of ozone. The system may accomplish this by using:

A manufacturing component, control components, measuring components, a reporting component and calculating component (such as an ozone generator, gas flow meter, fluid pump, variable pitch platform, data acquisition device, inlet ozone concentration monitor, and exit ozone concentration monitor) that cooperate to manufacture and deliver a measured, controlled, accurate and reproducible amount of ozone, the delivered-ozone, to a fluid through the use of a gas-fluid contacting device that provides for the interface between the ozone/oxygen admixture and fluid. Using control components, measuring components, a reporting component and calculating component (such as a gas flow meter, fluid pump, variable pitch platform, data acquisition device, inlet ozone concentration monitor, and exit ozone concentration monitor) that cooperate, the system may instantly differentiate the delivered-ozone from the absorbed-dose of ozone.

The system utilizes (for example, a gas flow meter, fluid pump, variable pitch platform, data acquisition device, inlet ozone concentration monitor, and exit ozone concentration monitor) control components, measuring components, a reporting component and calculating component that cooperate and instantly report data that may include the delivered-ozone, residual-ozone, absorbed-dose of ozone, interface-time, elapsed-time, and, the amount and flow rate of the fluid delivered to the gas-contacting device.

1. Construction Materials

The gas-contacting surfaces of the ozone delivery system including gas-fluid contacting devices are constructed from ozone-inert materials to avoid consumption of ozone. Ozone-inert materials include stainless steel, borosilicate, quartz, ceramic composites, PFA (copolymer of tetrafluoroethylene and perfluorinated vinyl ether from the perfluoroalkoxy group) and PTFE (polytetrafluoroethylene, TEFLON), and are further defined as being non-reactive within the concentration range of ozone manufactured and delivered by an ozone delivery system. A delivery system including one or more gas-fluid contact devices may be constructed without the inclusion of any fluoropolymers, polyfluoroethylene, PFA or PTFE materials, in the event these materials become a health concern.

2. Gas Flow

Figure 1:
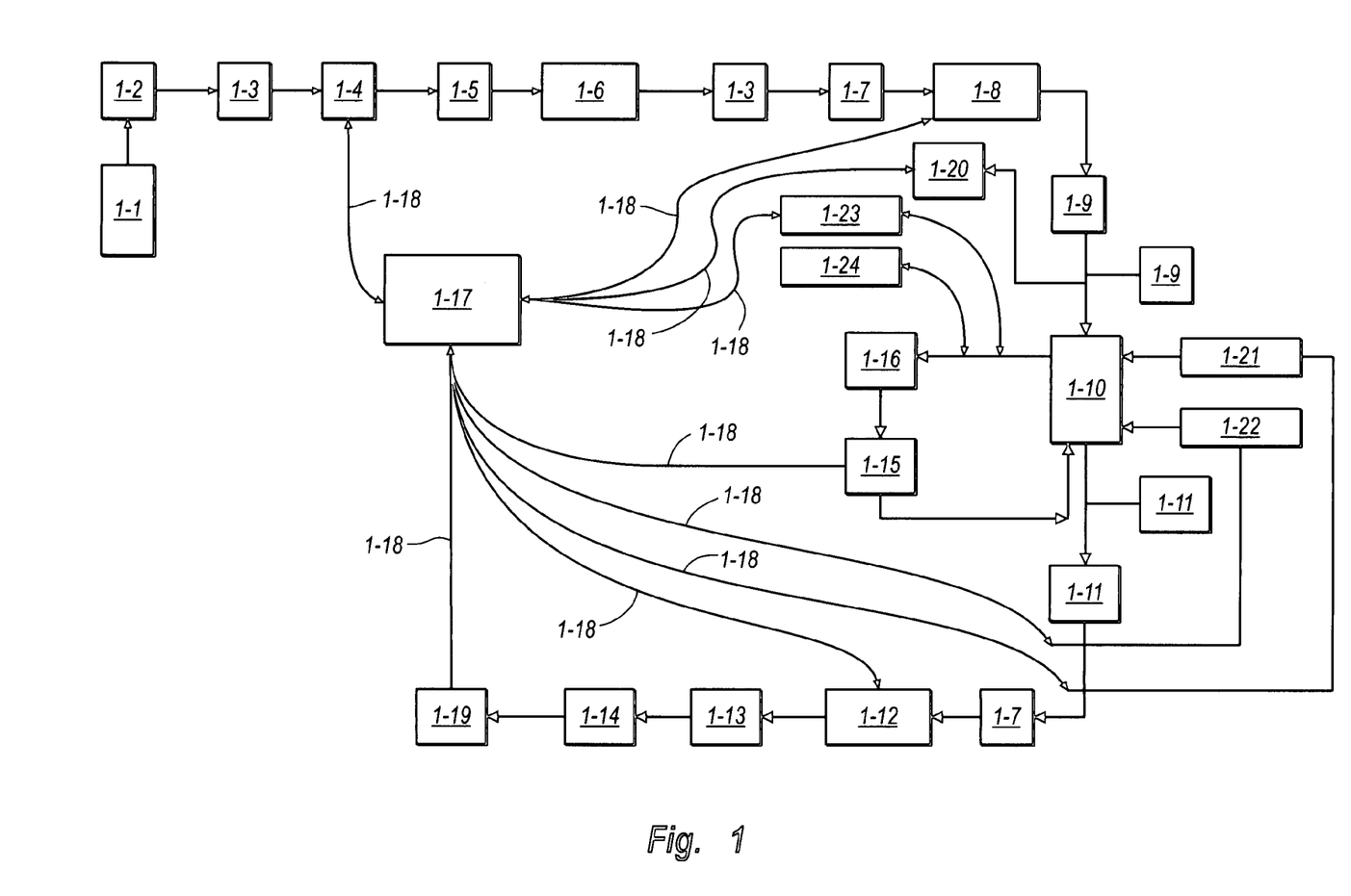
FIG. 1 illustrates a schematic diagram of the ozone delivery system described in the present invention.
Figure 4:
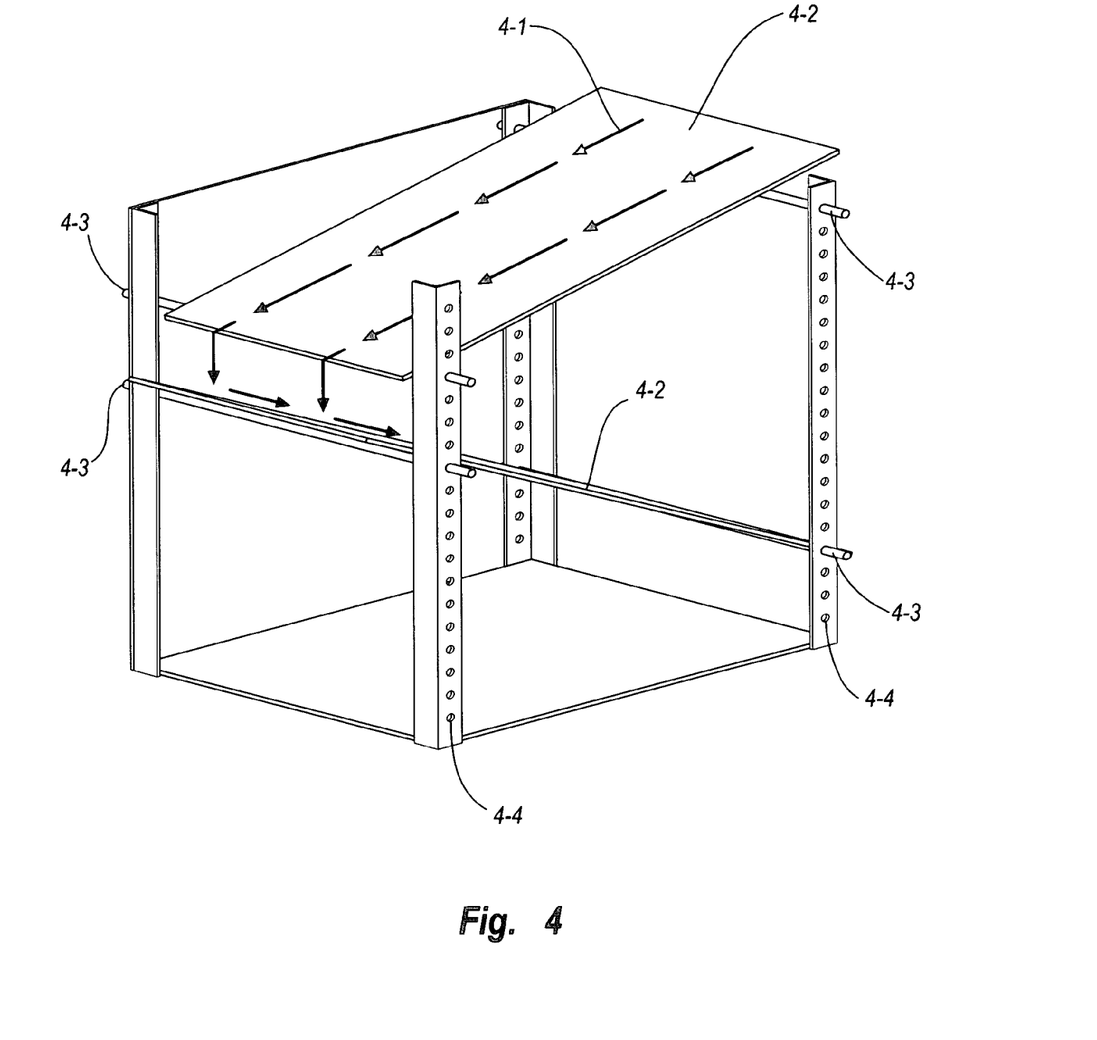
FIG. 4 illustrates a schematic diagram of a variable pitch platform used in conjunction with FIG. 3.

Medical grade oxygen is the source gas utilized, as lesser grades of oxygen may include nitrogenous contaminants resulting in the formation of toxic nitrous oxides. FIG. 1 illustrates that the oxygen flows from a pressurized cylinder (1-1), through a regulator (1-2), through a particle filter (1-3), through a flow meter (1-4) where the oxygen and subsequent ozone/oxygen admixture flow rate is controlled and measured, through a pressure release valve (1-5), through an ozone generator (1-6) wherein the concentration of the ozone/oxygen admixture is manufactured and controlled and where the admixture volume contains the delivered-ozone. The ozone/oxygen admixture flows through a particle filter (1-3) to remove particulates, and through an optional moisture trap (1-7), to reduce moisture. The admixture proceeds through an ozone inlet concentration monitor (1-8) that measures and reports the inlet ozone concentration of the ozone/oxygen admixture that contains the delivered-ozone. This real-time measurement may be based on ozone s UV absorption characteristics as a detection methodology. The ozone/oxygen admixture then passes through a set of valves (1-9) used to isolate a gas-fluid contacting device for purging of gasses. The ozone/oxygen admixture may pass an optional humidity sensor (1-20) where humidity may be measured and recorded, through a gas-fluid contacting device (1-10) where it interfaces with a fluid. The interface-time between an ozone/oxygen admixture and a fluid may be controlled through adjustment of the variable pitch platform as illustrated in FIG. 4, the fluid pump (1-15), and the time controlling capacity of the data acquisition device (1-17). The interface-time can be measured by the data acquisition device (1-17). Temperature and pressure may be measured by the use of temperature sensors (1-25) and pressure sensors (1-26), respectively, inserted into their respective temperature port (1-21) and pressure port (1-22). The resultant ozone/oxygen admixture containing the residual-ozone then exits the gas-fluid contacting device and flows through the exit purge valves (1-11), through a moisture trap (1-7), through an exit ozone concentration monitor (1-12), which may utilize a similar detection methodology as ozone concentration monitor (1-8), and that measures and reports the exit ozone/oxygen admixture concentration. The exiting ozone/oxygen admixture then proceeds through a gas drier (1-13), through an ozone destructor (1-14) and a flow meter (1-19).

3. Fluid Flow

Figure 5:
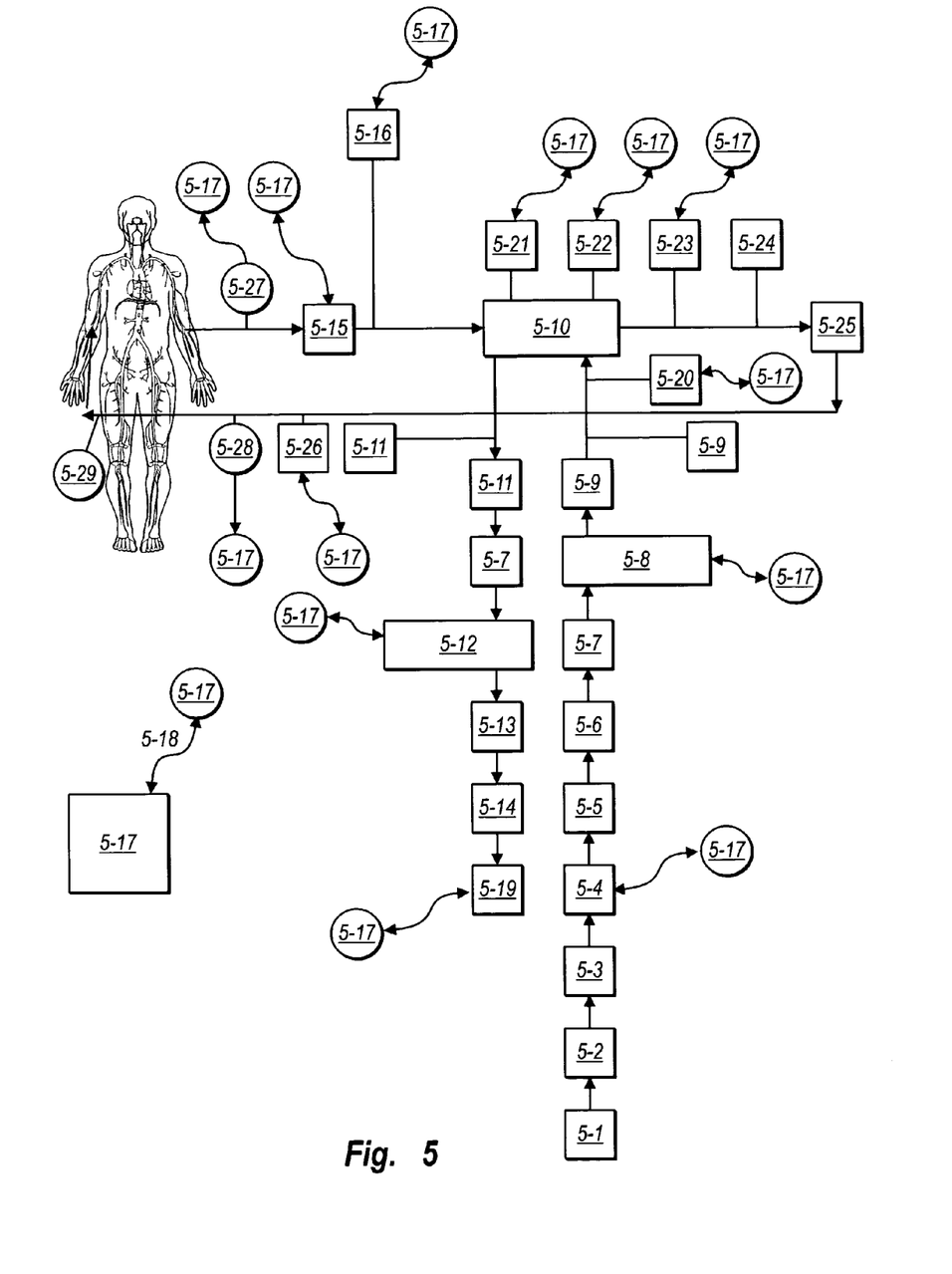
FIG. 5 illustrates a schematic diagram of a continuous loop configuration for fluid flow in a dialysis-like format.

FIG. 1 further illustrates that a fluid flows through tubing, from the fluid pump (1-15), into the gas-fluid contacting device (1-10) where it interfaces with an ozone/oxygen admixture containing the delivered-ozone. Insertion ports for temperature and pressure sensors may be located in the gas-fluid contacting device for the measurement of temperature and pressure, respectively. After interfacing with the ozone/oxygen admixture, the fluid exits into tubing that may contain a port for an optional absorbed oxygen sensor (1-23) followed by a fluid access port allowing for fluid removal (1-24) and into an optional reservoir (1-16), where if configured in a closed loop, the fluid is circulated in a repetitive manner. Other fluid loop configurations may be utilized, including but not limited to, configurations similar to a those used in dialysis for mammalian applications, for example as depicted in FIG. 5.

A data acquisition device (1-17), such as DAQSTATION (Yokogawa), for example, has time measurement capabilities, reports, stores and monitors data instantly and in real-time, and performs various calculations and statistical operations on data acquired. All data is transmitted to the data acquisition device through data cables (1-18), including: data from ozone concentration monitors (1-8) and (1-12), flow meters (1-4) and (1-19), humidity sensor (1-20), temperature sensor (1-21), pressure sensor (1-22), fluid pump (1-15), and absorbed oxygen sensor (1-23). The elapsed time, a composite of both the interface time and the period of time that the fluid circulates through the other elements of the apparatus can be measured and controlled through the data acquisition device (1-17).

4. Measurement of Delivered-Ozone, Residual-Ozone and Absorbed-Dose of Ozone

The ozone delivery system utilizes measuring components, reporting components and calculating components (such as inlet ozone concentration monitor, exit ozone concentration monitor, gas flow meter, fluid pump, data acquisition device) that cooperate together to determine certain calculated-data including the delivered-ozone, the residual-ozone and the absorbed-dose of ozone.

Delivered-ozone is an amount of ozone calculated by multiplying the measured volume of ozone/oxygen admixtures, as reported by gas flow meters, by the measured concentration of ozone within the ozone/oxygen admixture as it enters the gas-fluid contacting device, as reported by the inlet ozone concentration monitor. The measured volume of ozone/oxygen admixtures is calculated by multiplying the measured gas flow reported by gas flow meters, by the elapsed-time, as determined by the time measurement capability of the data acquisition device.

Residual-ozone is an amount of ozone calculated by multiplying the measured volume of ozone/oxygen admixtures, as reported by gas flow meters, by the measured concentration of ozone within the ozone/oxygen admixture exiting the gas-fluid contacting device, as reported by the exit ozone concentration monitor. The measured volume of ozone/oxygen admixtures is calculated by multiplying the measured gas flow reported by gas flow meters, by the elapsed-time, as determined by the time measurement capability of the data acquisition device.

The absorbed-dose of ozone is an amount of ozone calculated by subtracting the amount of residual-ozone from the amount of delivered-ozone, as determined by the time measurement capability of the data acquisition device.

The absorbed-dose of ozone may range from 1 to 10,000,000 micrograms per milliliter of fluid, and may be between 1 and 10,000 ug per milliliter of fluid.

All measured-data, including measured data from the gas flow meters, inlet and exit ozone concentration monitors, the fluid pump, temperature sensors, pressure sensors, absorbed oxygen sensor and humidity sensors are transmitted to a data acquisition device. The data acquisition device has time measuring capabilities, and instant, real-time reporting, calculating and data storing capabilities to process all measured data. The data acquisition device may use any measured data or any combination of measured data as variables to produce calculated-data. Examples of calculated-data may include delivered-ozone, residual-ozone, absorbed-dose of ozone, absorbed-dose of ozone per unit volume of fluid, and the absorbed-dose of ozone per unit volume of fluid per unit time.

5. Variables and Equipment

An ozone delivery system includes an ozone generator (1-6) for the manufacture and control of a measured amount of an ozone/oxygen admixture and where the admixture volume contains the delivered-ozone. A commercially available ozone generator capable of producing ozone in a concentration range between 10 and 3,000,000 ppmv of ozone in an ozone/oxygen admixture may be employed. Ozone/oxygen admixture concentrations entering the gas-fluid contacting device are instantly and constantly measured in real time, through an ozone concentration monitor (1-8) that may utilize UV absorption as a detection methodology. A flow meter (1-4) controls and measures the delivery of the delivered-ozone in an ozone/oxygen admixture to the gas-fluid contacting device at a specified admixture flow rate. Ozone/oxygen admixture flow rates are typically in the range between 0.1 and 5.0 liters per minute.

Measurement of the humidity of the ozone/oxygen admixture delivered to the gas-fluid contacting device may be included through the use of a humidity sensor. A humidity sensor port (1-20) may be provided in the ozone/oxygen admixture connecting tubing, however, it can be placed in a variety of locations. For example, the humidity sensor may be located in the connecting tubing prior to the admixture's entrance into gas-fluid contacting device.

Measurement of the temperature within the gas-fluid contacting device during the interface-time may be provided by inclusion of a temperature sensor port in the gas fluid contacting device through which a temperature sensor (1-21) may be inserted. The temperature at which ozone/oxygen admixtures interface fluids ranges from 4° to 100° C., and may be performed at ambient temperature, 25° C., for example. The temperature at which the interface occurs can be controlled by placing the gas-fluid contacting device, optional reservoir, and both gas and fluid connecting tubing in a temperature controlled environment, and/or by the addition of heating or cooling elements to the gas-fluid contact device.

Measurement of the pressure within the gas-fluid contacting device during the interface-time is provided by inclusion of a pressure sensor port in the gas-fluid contacting device through which a pressure sensor (1-22) may be inserted. The pressure at which an ozone/oxygen admixture interfaces with a fluid ranges from ambient pressure to 50 psi and may be performed between ambient pressure and 3 psi, for example. A pressure sensor port may be provided in each gas-fluid contacting device to measure and report the pressure at which the interface occurs.

The concentration of the ozone/oxygen admixtures exiting the gas-fluid contacting device and where the admixture volume contains the residual-ozone, are instantly and constantly measured in real time through an exit ozone concentration monitor that may utilize UV absorption as a detection methodology (1-12).

A fluid pump (1-15) controls and measures the flow rate of the fluid delivered to the gas-fluid-contacting device at a specified fluid flow rate. Fluid flow rates through the gas-fluid contacting device typically will range from 1 ml to 100 liters per minute, and for example, may be between 1 ml to 10 liters per minute. The fluid may be contained within a closed-loop design and may be circulated through the gas-fluid contacting device once or multiple times.

Measurement of the amount of oxygen absorbed into a fluid while it interfaces with the ozone/oxygen admixture within the gas-fluid contacting device may be provided through the use of an absorbed oxygen sensor. The sensor is inserted within the absorbed oxygen sensor port (1-23) located in the tubing as it exits the gas-fluid contacting device. Measurement of absorbed oxygen may be recorded in various units, including ppm, milligrams/liter or percent saturation.

The system also includes a fluid access port (1-24) for fluid removal. The port is generally located in the tubing member after the fluid exits through the fluid exit port of the gas-fluid contacting device and prior to the optional reservoir (1-16).

A data acquisition device (1-17), such as DAQSTATION (Yokogawa), for example, has time measurement capabilities, reports, stores and monitors data instantly and in real-time, and performs various calculations and statistical operations on data acquired. Data is transmitted to the data acquisition device through data cables (1-18), including: data from ozone concentration monitors (1-8) and (1-12), flow meters (1-4) and (1-19), humidity sensor (1-20), temperature sensor (1-21), pressure sensor (1 fluid pump (1-15) and absorbed oxygen sensor (1-23).

One of skill in the art will appreciate that components of an ozone delivery system may be replaced by those of technical equivalence.

Calculated-data may include delivered-ozone, residual-ozone, and the absorbed-dose of ozone. Measurement of the volume of the ozone/oxygen admixture delivered can be calculated though data provided from the flow meter (1-4) and the time measurement capability of the data acquisition device (1-17). Measurement of the volume of fluid delivered to the gas-fluid contacting device (1-10) can be calculated by the data acquisition device (1-17) utilizing fluid flow rate data transmitted from the fluid pump (1-4).

Figure 3:
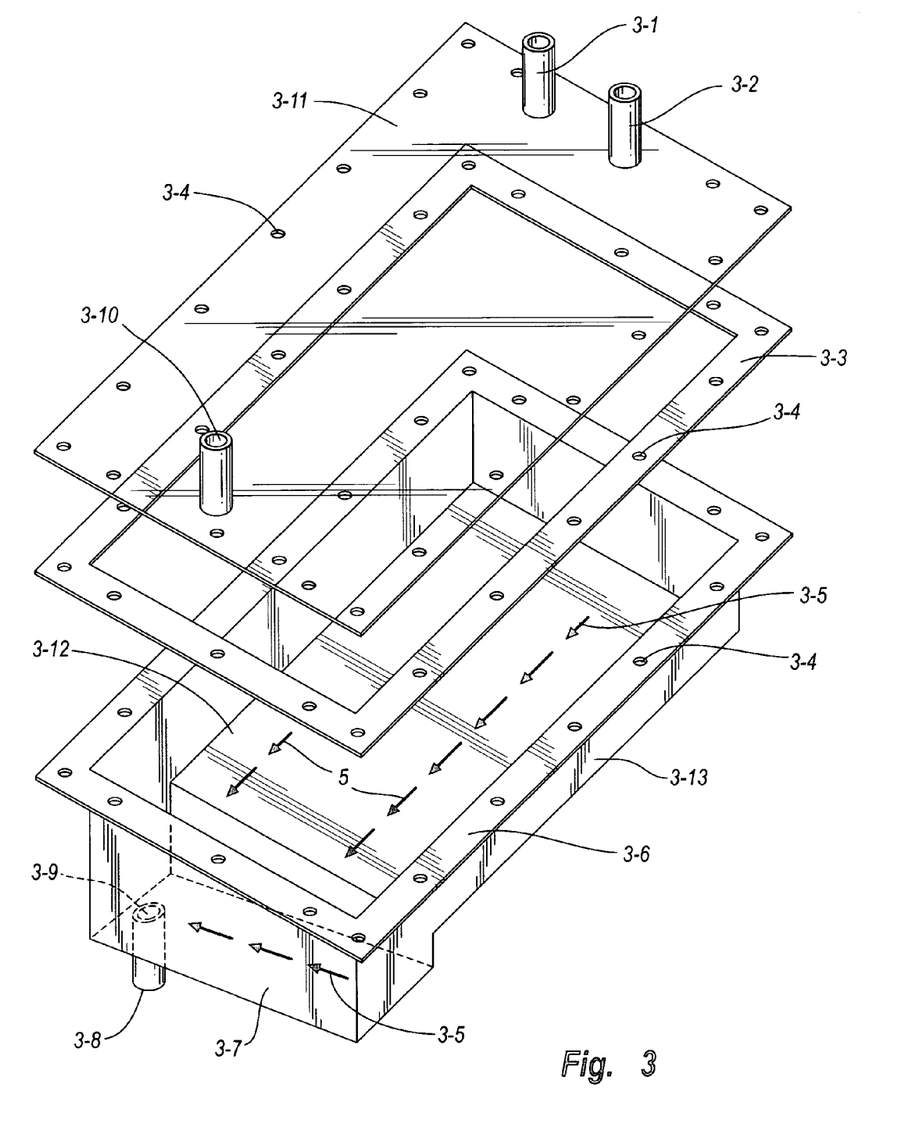
FIG. 3 illustrates a schematic diagram of a variable pitch gas-fluid contacting device.

The elapsed-time can be measured and controlled through the data acquisition device (1-17). The elapsed-time that the fluid circulates through the apparatus including the gas-fluid contacting device and is interfaced with an ozone/oxygen admixture can vary, generally for duration of up to 120 hours. The interface-time may also be measured by the time measuring capacity of the data acquisition device (1-17). The interface-time between a fluid and an ozone/oxygen admixture may be controlled through a composite of controls. These controls include: the angle of the gas fluid contacting device (as illustrated in FIGS. 3 and 4), the fluid flow rate via fluid pump, and the time controlling capacity of the data acquisition device. The interface-time may vary in duration of up to 720 minutes, and generally within duration of up to 120 minutes.

Controllable variables for an ozone delivery system may include: delivered amounts and concentrations of ozone in the entrance ozone/oxygen admixtures, admixture flow rates, fluid flow rates, admixture flow rates, temperature in the gas-fluid contacting device, interface-time between fluid and admixture; and, the elapsed-time that the fluid may circulate through the apparatus and interface with an ozone/oxygen admixture.

Measurable variables may include: ozone/oxygen admixture amounts and flow rates, amounts and concentrations of ozone in the entrance and exit ozone/oxygen admixtures, fluid flow rates, temperature and pressure in the gas-contacting device, humidity of the entrance admixture to the gas-fluid contacting device, absorbed oxygen by the fluid, interface-time and elapsed-time.

Data representing controllable variables and measurable variables acquired by the apparatus allows for a variety of calculations including: delivered-ozone, residual-ozone, absorbed-dose of ozone, absorbed-dose of ozone per unit volume of fluid, and the absorbed-dose of ozone per unit volume of fluid per unit time.

Continuous Loop Configuration

FIG. 5 illustrates blood from a patient being extracorporeally interfaced with an ozone/oxygen admixture. Blood may be circulated in a continuous loop format in a venovenous extracorporeal exchange format as will be appreciated by one of skill in the art. As an example, this continuous loop can be established through venous access of the antecubital veins of both right and left arms. Prior to establishing an extracorporeal circuit, a patient may optionally be anticoagulated with heparin or any other suitable anticoagulant known to those skilled in the art.

1. Gas Flow for Continuous Loop

The oxygen flows from a pressurized cylinder (5-1), through a regulator (5-2), through a particle filter (5-3) to remove particulates, through a flow meter (5-4) where the oxygen and subsequent ozone/oxygen admixture flow rate is controlled and measured. The oxygen proceeds through a pressure release valve (5-5), through an ozone generator (5-6) where the concentration of the ozone/oxygen admixture is manufactured and controlled and where the admixture volume includes the delivered-ozone. The ozone/oxygen admixture flows through an optional moisture trap (5-7), to reduce moisture. The admixture proceeds through an inlet ozone concentration monitor (5-8) that measures and reports the inlet ozone concentration of the ozone/oxygen admixture that contains the delivered-ozone. This real-time measurement may be based on ozone's UV absorption characteristics as a detection methodology. The ozone/oxygen admixture then passes through a set of valves (5-9) used to isolate a gas-fluid contacting device for purging of gasses. The ozone/oxygen admixture may pass an optional humidity sensor (5-20) where humidity may be measured and recorded, and into a gas-fluid contacting device (5-10) where it interfaces with fluid. The interface-time between fluid and ozone/oxygen admixture may be controlled through adjustment of the variable pitch platform as illustrated in FIG. 4, fluid pump (5-15) and the time controlling capacity of the data acquisition device (5-17). The interface-time may then be measured by the data acquisition device (5-17). Temperature (5-21) and pressure (5-22) may be measured by the use of optional temperature and pressure sensors, respectively, inserted into their respective ports. The resultant ozone/oxygen admixture containing the residual-ozone exits the gas-fluid contacting device and flows through the exit purge valves (5-11), through a moisture trap (5-7), through an exit ozone concentration monitor (5-12), which may utilize a similar detection methodology as the inlet ozone concentration monitor (5-8), that measures and reports the exit ozone/oxygen admixture concentration. The exiting ozone/oxygen admixture then proceeds through a gas drier (5-13), through an ozone destructor (5-14) and a flow meter (5-19).

2. Fluid Flow for Continuous Loop

Intravenous blood flows from the patient through tubing through a pressure gauge (5-27), which monitors the pressure of the blood flow exiting the patient. Generally, the pressure of the blood exiting the patient ranges from a negative pressure of 100-200 mm Hg, and may be between a negative pressure of 150 and 200 mm Hg, with a maximum cutoff pressure of minus 250 mm Hg. The blood flows through a fluid pump (5-15) and is optionally admixed with heparin or other suitable anticoagulant as provided by an optional heparin pump (5-16). The blood then passes through the gas-fluid contacting device (5-10) where it interfaces with the ozone/oxygen admixture containing the delivered-ozone. Ports for the insertion of sensors may be located in the gas-fluid contacting device for the measurement of temperature and pressure, respectively. After interfacing with the ozone/oxygen admixture, the fluid exits into tubing that may contain a port for an optional absorbed oxygen sensor (5-23) followed by a fluid access port (5-24). The blood continues through an air/emboli trap (5-25) that removes any gaseous bubbles or emboli. The blood then continues through a fluid pump (5-26) and then into a pressure gauge (5-28) which monitors the pressure of the blood flow before returning to the patient. Generally, the pressure of the blood entering the patient ranges from a pressure of 100-200 mm Hg, and may be between 150 and 200 mm Hg, with a maximum cutoff pressure of 250 mm Hg. The blood continues through a priming fluid access port (5-29) that allows for the removal of the priming fluid from the extracorporeal loop. The blood is then re-infused directly into the patient.

A data acquisition device (5-17), such as DAQSTATION (Yokogawa), for example, has time measurement capabilities, reports, stores and monitors data instantly and in real-time, and performs various calculations and statistical operations on data acquired. All data is transmitted to the data acquisition device through data cables (5-18), including: data from ozone concentration monitors (5-8) and (5-12), flow meters (5-4) and (5-19), humidity sensor (5-20), temperature sensor (5-21), pressure sensor (5-22), fluid pumps (5-15) and (5-26), pressure gauges (5-27) and (5-28) and absorbed oxygen sensor (5-23). The elapsed time, a composite of both the interface time and the period of time that the fluid circulates through the other elements of the apparatus can be measured and controlled through the data acquisition device (5-17).

Other possible configurations for an extracorporeal blood circuit known to those skilled in the art are included within the spirit of this disclosure.

Gas-Fluid Contacting Devices

One or more gas-fluid contacting devices may be included in an ozone delivery system to increase the surface area of a fluid to be treated allowing for an increase in the mass transfer efficiency of the ozone/oxygen admixture. Gas-fluid contacting devices may encompass the following properties: closed and isolated from the ambient atmosphere, gas inlet and outlet ports for the entry and exit of ozone/oxygen admixtures, fluid inlet and outlet ports for the entry and exit of a fluid. They may also include measuring components (such as a temperature sensor, pressure sensor and data acquisition device) for the measurement and reporting of temperature and pressure within a gas-fluid contacting device. These devices may generate a thin film of the fluid as it flows within a gas-fluid contacting device, and may be constructed from ozone-inert construction materials including, quartz, ceramic composite, borosilicate, stainless steel, PFA and PTFE.

Gas-fluid contacting devices include designs that encompass surfaces that may be horizontal or approaching a horizontal orientation. These surfaces may include ridges, indentations, undulations, etched surfaces or any other design that results in a contour change and furthermore, may include any pattern, regular or irregular, that may disrupt the flow, disperse the flow or cause turbulence. These surfaces may or may not contain holes through which a fluid passes through. The surface of the structural elements may have the same or different pitches. Designs of gas-fluid contacting devices may include those that involve one or more of the same shaped surfaces or any combination of different surfaces, assembled in any combination of ways to be encompassed within the device may include cones, rods, tubes, flat and semi-flat surfaces, discs and spheres.

The interface between an ozone/oxygen admixture and a fluid may be accomplished by the use of a gas-fluid contact device that generates a thin film of the fluid that interfaces with the ozone-oxygen admixture as it flows through the device. One of skill in the art will appreciate that generation of any interface that increases the surface area of the fluid and thereby maximizes the contact between a fluid and an admixture, may be used. Additional examples include the generation of an aerosol through atomization or nebulization.

The interface-time within a gas-fluid contacting device is measurable, controllable, calculable and reportable. Furthermore, the interface-time may be for duration of up to 720 minutes, generally however, for duration of up to 120 minutes. Following the interface-time, the fluid exits the gas-fluid contacting device containing the absorbed-dose of ozone. The elapsed-time, a composite of both the interface-time and the time for circulation of a fluid through other elements of an ozone delivery system is also measurable, controllable, calculable and reportable. This elapsed-time is for duration of up to 120 hours.

The pressure at the interface between fluid and ozone/oxygen admixture within a gas-fluid contacting device may be measured. Measurement of pressure within the device may be accomplished through the use of a pressure sensor inserted at the pressure port of the gas-fluid contacting device. The pressure at which an ozone/oxygen admixture interfaces with a fluid ranges from ambient pressure to 50 psi and may be performed between ambient pressure and 3 psi.

The temperature within a gas-fluid contacting device may be controlled by housing the device such that the connecting tubing containing both gas and fluid and an optional reservoir are maintained in a controlled temperature environment. A flow hood that provides for temperature regulation is an example of a controlled temperature environment. Alternatively, the addition of heating or cooling elements to the gas-fluid contact device may provide for the control of temperature. Measurement of temperature within the device may be accomplished through the use of a temperature sensor inserted at the temperature port of a gas-fluid contacting device. The temperature at which ozone/oxygen admixtures interface fluids ranges from 4° to 100° C., and may be performed at ambient temperature, 25° C., for example.

A gas-fluid contacting device may be placed onto any type of agitator platform. The agitator platform may be employed to increase the effectiveness of the ozone/oxygen admixture interface with a fluid being passed through the device.

Gas-fluid contacting devices may be utilized individually or in conjunction with other such devices, whether they are similar or dissimilar in construction, design or orientation. In the event that multiple devices are utilized, either of the same design, or a combination of different gas-fluid contacting devices of different designs, these devices may be arranged one after the other in succession (in series), making a single device out of multiple individual contact devices.

In a series configuration of devices, a fluid flowing through the different contact devices flows in series, from the fluid exit port of one contact device to the fluid entrance port of the next, until passing through all the devices. The ozone/oxygen admixture may flow in a number of arrangements. In one example, the ozone/oxygen admixture flows through different contact devices in series, from the admixture exit port of one contact device to the admixture entrance port of the next. As an alternative example, the ozone/oxygen admixture may flow directly from the admixture source to the entrance port of each different contact device. Another alternative is a combination of the foregoing examples where the ozone/oxygen admixture flows from the exit port of some devices to the entrance port of other devices and in addition, to the entrance of some devices directly from the admixture source. In the event that multiple devices are utilized, the resultant fluid from the terminal device can either be collected or returned to the original device and recirculated.

1. Sphere-Containing Gas-Fluid Contacting Device

Figure 2:
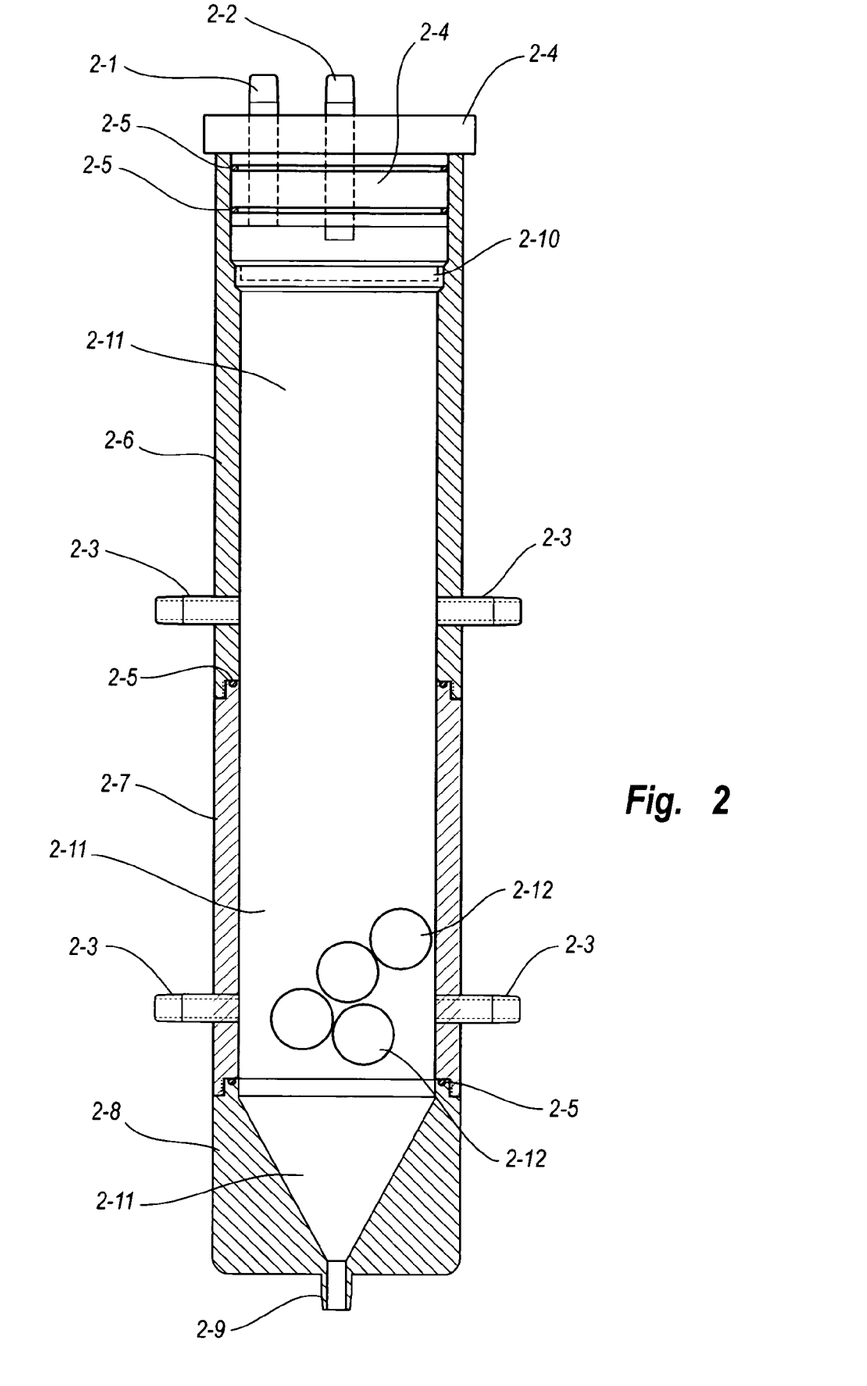
FIG. 2 illustrates a schematic diagram of a sphere-containing gas-fluid contact device.

A gas-fluid contacting device, as illustrated in FIG. 2, may consist of an upper housing (2-6), a middle housing of variable thickness (2-7), and a lower housing (2-8) of various dimensions with regard to height and internal diameter. One of skill in the art will appreciate that a disparity in dimension is provided for the applicability of a gas-fluid contacting device to fluids of varying volume and viscosity. The device housing includes at least one inlet (2-3) and one exit port (2-1) for ozone/oxygen admixture entrance and exit, respectively.

A fluid entrance port (2-2) is positioned at the top of the device permitting entrance and fluid flow is directed in a downward fashion. The top of the device is constructed with a removable cap (2-4) sealed with ozone-inert O-rings (2-5). The ozone/oxygen admixture may flow in a direction similar, counter or in combination thereof to the direction of the fluid flow. A fluid exit port (2-9) may be positioned at the base of the device. Temperature and pressure ports may be included for insertion of temperature and pressure sensors, respectively.

A gas-fluid contacting device may be filled with a number of spheres (2-12), generally of quartz, ceramic composite, borosilicate, PFA or PTFE construction. These spheres may generally range in diameter from 1 to 100 mm, although one of skill in the art will recognize that alternative diameters are possible depending on need. The sphere content and configuration within the cartridge may include; homogenous spherical diameter, heterogeneous spherical diameter, continuous gradient of increasing spherical diameter, continuous gradient of decreasing spherical diameter and discontinuous sets of spheres wherein each set of spheres is of homogenous size but sphere size disparity may exist between the plates.

Regardless of spherical diameter and distribution configuration, the spheres generally occupy approximately seventy-five percent of the internal volume of the device (2-11), however, one of skill in the art will appreciate that alternative volumes are possible. Generally, the total interface surface area of the sphere-containing gas-fluid contacting device can range from 0.01 $m^2$ upwards depending on the size of the device, and the sphere diameter chosen. A disk/tray (2-10) may be located above the spheres and is perforated to permit a more homogenous distribution of the fluid across the spherical surfaces upon entrance into the device.

The fluid enters the device from the fluid entrance port (2-2) and flows over the surface of these spheres forming a thin film over the surface of each, and causing turbulence as the fluid flows down through the device. Increasing the surface area of the fluid, by generating a thin film, for example, permits for the maximization of mass transfer of the ozone/oxygen admixture that continuously passes over each sphere. The fluid exits the device through the fluid exit port (2-9).

2. Cylindrical Rod Containing Device

A cylindrical rod-containing device contains a number of cylindrical rods, either solid or hollow in design, whose construction may include quartz, ceramic composite or borosilicate. These rods may generally range in diameter between 3-25 mm but may vary significantly in applications with larger volumes of fluid or different viscosities. In addition, these rods may be constructed with ridges, undulations, indentations or etched surfaces along their length, respectively. The cylindrical rods are secured in place within a housing to maintain a relative equidistance from adjoining rods and the internal walls of the housing.

A fluid entrance port is positioned at the top of the device permitting entrance of a fluid such that flow is gravity directed. Atop the cylindrical rods is a disk that is perforated to permit a more homogenous distribution of the fluid as it enters the device and along the surfaces of both the cylindrical rods and the internal walls of the device housing.

The number of rods contained within a device may vary based upon the interface surface area desired. The total interface surface area of this example gas-fluid contacting device approximates 1.0 $m^2$/meter length of the device or greater depending on the size of the device and the number of rods chosen. Furthermore, one of skill in the art will appreciate that the interface surface area can be substantially increased by incorporating hollow cylindrical (tubes) rods thereby creating a surface area approximating 1.5 $m^2$/meter length of the device.

3. Variable Pitch Device

A gas-fluid contacting device, as illustrated in FIG. 3, may include an enclosed chamber, generally rectangular in shape, whose dimensions may vary based on the interface surface area desired. A fluid enters the device and flows over the bottom surface (3-12) of the chamber to form a thin film. The bottom surface (3-12) may include flat, undulating or ridged designs, may be etched, and may have regular or irregular patterns of any shape or form that disrupt and/or disperse the fluid flow. At the fluid entrance of the device (3-2), construction allows the fluid to distribute evenly along the leading edge of the bottom surface. In contrast, the fluid exit end is constructed with a fluid collection trough (3-7) that is graded toward the drain (3-9) to permit collection of the fluid for exiting. Fluid entrance (3-2) and exit ports (3-8) are positioned at opposite ends of the device.

Fluid flow may be gravity directed (3-5). The top cover (3-11) of the device is secured to the bottom of the device by a flange (3-6) on the base, and uses an ozone-inert gasket (3-3) between the top (3-11) and bottom (3-13) and is attached to the bottom through the use of fasteners that pass through the holes (3-4) in the top cover (3-11), the gasket (3-3), and bottom flange (3-6). One skilled in the art will recognize different sealing and attachment technologies may be employed to attach and seal the top to the bottom, and the method described serves only as an example that should not be considered limiting in scope. The ozone/oxygen admixture may enter the device through the gas inlet port (3-10), and exit the device through the gas exit port (3-1), although these may be reversed depending on the desired direction of the gas flow. The gas may flow in a direction similar, counter or in combination thereof to the direction of the fluid flow. The gas-fluid interface-time is controllable by varying a number of parameters, including adjusting the pitch on a variable pitch platform (See FIG. 4). The pitch is adjustable ranging from 0° (horizontal) to 90° (vertical).

The device exhibited in FIG. 3 can assume a variety of pitches through the use of the platform detailed in FIG. 4. A single or multitude of variable pitch devices (4-2) can be assembled in series on this platform (4-4) that also provides an adjustment mechanism to provide individual pitch variation for each device. The platform has a variety of positions for support rods (4-3) to be inserted on which each device is supported that allows for the variety of pitch desired and resultant fluid flow (4-1).

When arranged in series with other contact devices, interface time between the fluid and ozone/oxygen admixture is controllable, and can be adjusted based on the individual pitch chosen for each device in series, or by adding additional devices to the series. The overall interface surface area will range from 0.01 $m^2$ for an individual device, and upwards based on the number of devices serially utilized.

Example 1

An example of data measured and calculated by the ozone delivery system that utilizes a fluid target described herein is included in Table 1. Newborn Calf Serum commercially obtained was utilized as the target fluid. The variable pitch device (FIG. 3) with variable pitch platform (FIG. 4) was employed as the gas-fluid contacting device. The following initial conditions were utilized; 300 ppmv ozone inlet concentration, 145 ml initial fluid volume, 1000 ml per minute gaseous flow rate, 189 ml per minute fluid flow rate counter current to the ozone/oxygen admixture flow. Incremental reductions in fluid volume are due to sampling of fluid through the fluid access port (24).

TABLE 1

NEWBORN CALF SERUM

MEASURED VARIABLES

| Elapsed-time (5 min intervals) | Fluid Volume (milliliters) | Gas Flow Rate (liters/minute) | Fluid Flow Rate (liters/minute) | Average Inlet Ozone Concentration (ppmv) | Average Exit Ozone Concentration (ppmv) |
|---|---|---|---|---|---|
| 5  | 145 | 0.998 | 0.189 | 305.2 | 38.2 |
| 10 | 143 | 0.972 | 0.189 | 361.5 | 40.4 |
| 15 | 141 | 1.000 | 0.189 | 312.7 | 20.6 |
| 20 | 139 | 1.000 | 0.189 | 314.0 | 37.3 |

CALCULATED VARIABLES

| Elapsed-time (minutes) | Average Differential Ozone Concentration (ppmv) | Delivered-ozone (ug) | Residual-ozone (ug) | Ozone Absorbed per Interval (ug) | Absorbed-dose of Ozone (ug) |
|---|---|---|---|---|---|
| 5  | 267.0 | 3.26E+03 | 4.08E+02 | 2.86E+03 | 2.86E+03 |
| 10 | 321.1 | 7.02E+03 | 8.28E+02 | 3.34E+03 | 6.20E+03 |
| 15 | 292.1 | 1.04E+04 | 1.06E+03 | 3.12E+03 | 9.32E+03 |
| 20 | 276.7 | 1.37E+04 | 1.46E+03 | 2.96E+03 | 1.23E+04 |

Example 2

An additional example of data measured and calculated by the system described herein is tabulated in Table 2 below. Newborn Calf Serum commercially obtained was utilized as the target fluid. The variable pitch device (FIG. 3) with variable pitch platform (FIG. 4) was employed as the gas-fluid contacting device. The following initial conditions were utilized; 600 ppmv ozone inlet concentration, 137 ml initial fluid volume, 1000 ml per minute gaseous flow rate, 189 ml per minute fluid flow rate counter current to the ozone/oxygen admixture flow. Incremental reductions in fluid volume are due to sampling of fluid through the fluid access port (24).

Example 3

Another example of data measured and calculated by the system described herein is tabulated in Table 3 below. Newborn Calf Serum commercially obtained was utilized as the target fluid. The variable pitch device (FIG. 3) with variable pitch platform (FIG. 4) was employed as the gas-fluid contacting device. The following initial conditions were utilized; 900 ppmv ozone inlet concentration, 145 ml initial fluid volume, 1000 ml per minute gaseous flow rate, 189 ml per minute fluid flow rate counter current to the ozone/oxygen admixture flow. Incremental reductions in fluid volume are due to sampling of fluid through the fluid access port (24).

TABLE 2

NEWBORN CALF SERUM

MEASURED VARIABLES

| Elapsed-time (5 minute intervals) | Fluid Volume (milliliters) | Gas Flow Rate (liters/minute) | Fluid Flow Rate (liters/minute) | Average Inlet Ozone Concentration (ppmv) | Average Exit Ozone Concentration (ppmv) |
|---|---|---|---|---|---|
| 5 | 137 | 1.000 | 0.189 | 604.2 | 72.0 |
| 5 | 135 | 1.000 | 0.189 | 609.6 | 63.5 |
| 5 | 133 | 1.000 | 0.189 | 606.6 | 70.8 |
| 5 | 131 | 1.000 | 0.189 | 605.3 | 71.7 |

CALCULATED VARIABLES

| Elapsed-time (minutes) | Average Differential Ozone Concentration (ppmv) | Delivered-ozone (ug) | Residual-ozone (ug) | Ozone Absorbed per Interval (ug) | Absorbed-dose of ozone (ug) |
|---|---|---|---|---|---|
| 5  | 532.2 | 6.47E+03 | 7.70E+02 | 5.69E+03 | 5.69E+03 |
| 10 | 546.1 | 1.30E+04 | 1.45E+03 | 5.84E+03 | 1.15E+04 |
| 15 | 535.8 | 1.95E+04 | 2.21E+03 | 5.73E+03 | 1.73E+04 |
| 20 | 533.6 | 2.60E+04 | 2.98E+03 | 5.71E+03 | 2.30E+04 |

TABLE 3

NEWBORN CALF SERUM

MEASURED VARIABLES

| Elapsed-time (5 minute intervals) | Fluid Volume (milliliters) | Gas Flow Rate (liters/minute) | Fluid Flow Rate (liters/minute) | Average Inlet Ozone Concentration (ppmv) | Average Exit Ozone Concentration (ppmv) |
|---|---|---|---|---|---|
| 5 | 145 | 1.000 | 0.189 | 908.1 | 68.0 |
| 5 | 143 | 1.000 | 0.189 | 911.4 | 50.1 |
| 5 | 141 | 1.000 | 0.189 | 904.4 | 46.6 |
| 5 | 139 | 1.000 | 0.189 | 904.7 | 50.9 |

CALCULATED VARIABLES

| Elapsed-time (minutes) | Average Differential Ozone Concentration (ppmv) | Delivered-ozone (ug) | Residual-ozone (ug) | Ozone Absorbed per Interval (ug) | Absorbed-dose of ozone (ug) |
|---|---|---|---|---|---|
| 5 | 840.1 | 9.72E+03 | 7.28E+02 | 8.99E+03 | 8.99E+03 |
| 10 | 861.3 | 1.95E+04 | 1.26E+03 | 9.22E+03 | 1.82E+04 |
| 15 | 857.8 | 2.92E+04 | 1.76E+03 | 9.18E+03 | 2.74E+04 |
| 20 | 853.8 | 3.88E+04 | 2.31E+03 | 9.13E+03 | 3.65E+04 |

Non-Fluid Target

In an alternative embodiment, the ozone delivery system is used for non-fluid targets. In this embodiment, a gas-fluid contacting device is not employed but rather a contact device applicable to a non-fluid target surface. The ozone delivery system is able to measure, control and report the amount of delivered-ozone, and measure, control and report the absorbed-dose of ozone. For medicinal applications, this embodiment is capable of measuring, reporting and differentiating the amount of delivered-ozone to the target from the absorbed-dose of ozone that is actually utilized by the target.

Examples of non-fluid targets for the delivered-ozone include: external limbs, and, any external tissue surface, including hard, soft and mucosal tissue targets of animals including humans. Internal tissues exposed through a variety of ways, including surgery and trauma may be interfaced with the delivered-ozone. Other targets for the delivered-ozone include: medical implements and instruments, foodstuffs, food handling and storage equipment, pharmaceutical and biological handling and storage equipment, air exchange and conditioning surfaces, microchips and other semi-conductor industry devices.

In this embodiment, an ozone delivery system includes manufacturing, control, measuring, reporting and calculating components (such as an ozone generator, gas flow meter, data acquisition device, inlet ozone concentration monitor, exit ozone concentration monitor) that cooperate together with a contact device for interfacing the delivered-ozone with the target. All gas-contacting surfaces in the system are constructed from ozone-inert construction materials. The structure of the contact device includes: dimensions sufficient to enclose the target, construction design allowing for the enclosed target to be sealed from the external environment, an inlet port for the entrance of the delivered-ozone in an ozone/oxygen admixture, and an exit port for the exit of residual-ozone. In addition, ports for the insertion of sensors to monitor pressure and temperature within the contact device while the delivered-ozone interfaces with the target are optionally provided.

Figure 6:
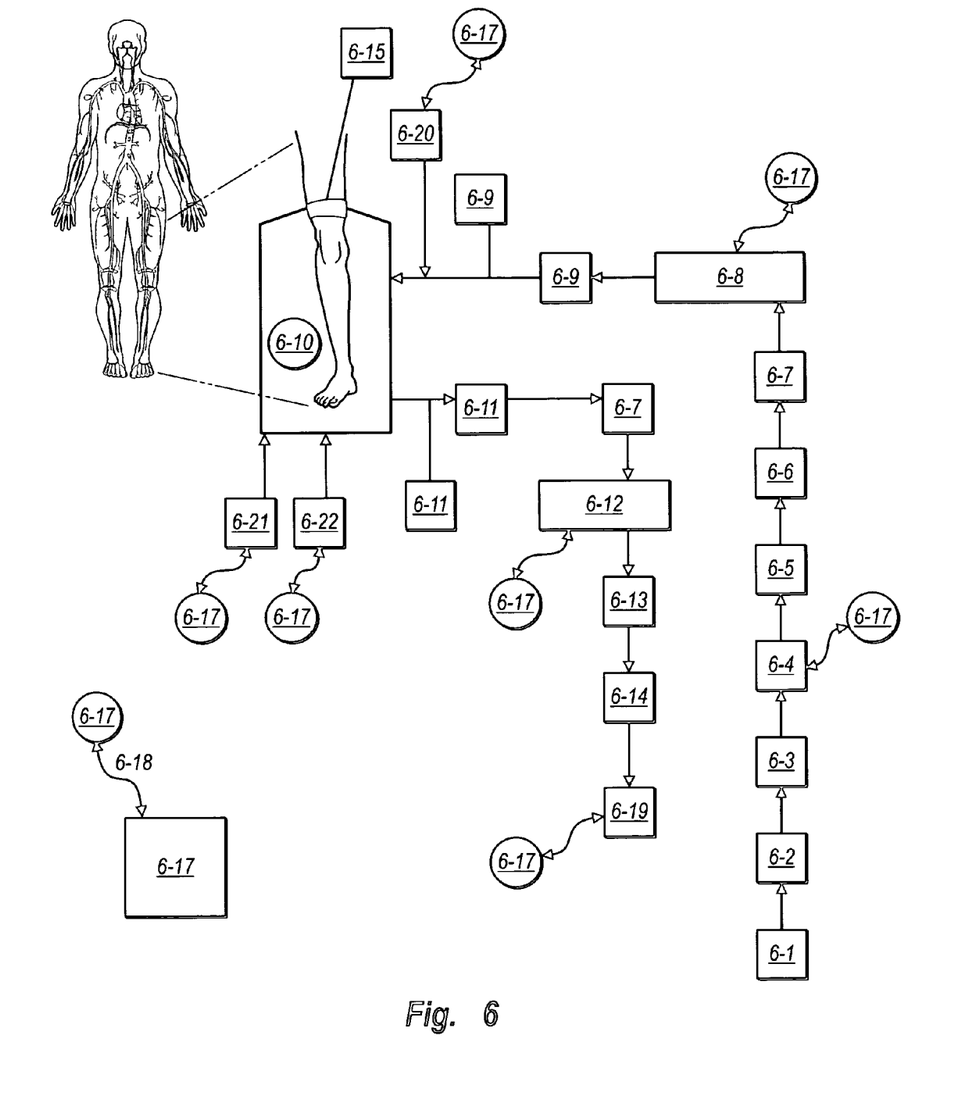
FIG. 6 illustrates a schematic diagram of a non-fluid topical application.

In one example a limb of a patient represents an irregular target surface for delivery of the delivered-ozone in a measured amount of an ozone/oxygen admixture, as illustrated in FIG. 6. The oxygen flows from a pressurized cylinder (6-1), through a regulator (6-2), through a particle filter (6-3) to remove particulates, through a flow meter (6-4) where the oxygen and subsequent ozone/oxygen admixture flow rate is controlled and measured. The oxygen proceeds through a pressure release valve (6-5), through an ozone generator (6-6) where the concentration of the ozone/oxygen admixture is manufactured and controlled and where the admixture volume comprises the delivered-ozone. The ozone/oxygen admixture flows through an optional moisture trap (6-7), to reduce moisture. The admixture proceeds through an inlet ozone concentration monitor (6-8) that measures and reports the inlet ozone concentration of the ozone/oxygen admixture volume that contains the delivered-ozone. This real-time measurement may be based on ozone's UV absorption characteristics as a detection methodology.

The ozone/oxygen admixture then passes through a set of valves (6-9) used to isolate a contact device for purging of gasses. The ozone/oxygen admixture may pass an optional humidity sensor (6-20) where humidity may be measured and recorded, and into a contact-device (6-10) where it is interfaced with the irregular target surface. In one example, the contact device is a 'bag-like' structure with the capability to accommodate the irregular contour of the limb. Examples of alternative contacting devices may include chambers of various dimensions, and flexible wrappings or coverings that encompass and contour to the irregularity of a target and includes a closure mechanism for sealing the target from the external environment.

A closure mechanism (6-15) at the site where the limb enters the contact device is provided sealing the enclosed portion of the limb from the environment. The variety of closure mechanisms included within the scope of the disclosure are known to those skilled in the art. The interface-time between the target surface and ozone/oxygen admixture is controlled and measured during the period that the target surface resides in the contact device through control of the time controlling capacity of the data acquisition device (6-17). Temperature (6-21) and pressure (6-22) may be measured by the use of optional sensors inserted into their respective ports. The resultant ozone/oxygen admixture containing the residual-ozone then exits the contact device and flows through the exit purge valves (6-11), through a moisture trap (6-7), through an exit ozone concentration monitor (6-12), which may utilize a similar detection methodology as ozone concentration monitor (6-8), and that measures and reports the exit ozone/oxygen admixture concentration containing the residual-ozone. The exiting ozone/oxygen admixture then proceeds through a gas drier (6-13), through an ozone destructor (6-14) and a flow meter (6-19).

A data acquisition device (6-17), such as DAQSTATION (Yokogawa), for example, reports, stores and monitors data instantly and in real-time, and performs various calculations and statistical operations on data acquired. Data is transmitted to the data acquisition device through data cables (6-18), including: data from ozone concentration monitors (6-8) and (6-12), flow meters (6-4) and (6-19), humidity sensor (6-20), temperature sensor (6-21), and pressure sensor (6-22). The 'elapsed-time' for this application is equivalent to the interface time. Other possible configurations for non-fluid topical applications through the use of a contact-device are included within the spirit of this disclosure.

According to this non-fluid embodiment, the ozone delivery system delivers an ozone/oxygen admixture containing a measured, controlled and reported amount of delivered-ozone, which enters the inlet port of the contact device encompassing the target. The target interfaces with the delivered-ozone over an elapsed-time where the absorbed-dose of ozone, the amount of ozone absorbed and utilized by the target, is measured, controlled and reported. The residual-ozone is contained within the ozone/oxygen admixture that exits through the exit port of the device. Variations in this embodiment include the measurement of temperature and pressure during the elapsed time for the interface between the target and delivered-ozone.

The present system may be embodied in other specific forms without departing from its spirit or essential characteristics. The described embodiments are to be considered in all respects only as illustrative and not restrictive. The scope of the system and method of use is, therefore, indicated by the appended claims rather than by the foregoing description. All changes which come within the meaning and range of equivalency of the claims are to be embraced within their scope.

What is claimed is:

1. An apparatus for delivering a measurable absorbed-dose of ozone to a measured amount of fluid, comprising:
    a) an ozone generator that manufactures an ozone/oxygen admixture, and controls the concentration of ozone within the ozone/oxygen admixture;
    b) a gas flow meter that controls and measures the amount and flow rate of the ozone/oxygen admixture delivered to a gas-fluid contacting device;
    c) a gas-fluid contacting device including at least one variable pitch device, each variable device including a base having a flange extending around an open upper end thereof, a cover closing the open upper end of said base, and a plurality of bolts extending through the cover and flange to removably attach the cover to the base, the base and the cover together defining an enclosed chamber having an inlet end and an outlet end and that interfaces an ozone/oxygen admixture with a fluid, wherein a gas exit port and a fluid entrance port are disposed in the cover proximate said inlet end, a gas inlet port is disposed in the cover proximate said outlet end, and a fluid drain port is disposed in said base at proximate said outlet end;
    d) a fluid pump that controls and measures an amount of the fluid and a flow rate of the fluid entering a the gas-fluid contacting device;
    e) a variable pitch platform for supporting the at least one variable pitch device, wherein said variable pitch platform includes a mechanism for adjusting the pitch of the at least one variable pitch device relative to a horizontal base of said platform, said variable pitch platform cooperating with the fluid pump to control the time during which the ozone/oxygen admixture interfaces with the fluid in the gas-fluid contacting device;
    f) an inlet ozone concentration monitor that measures the concentration of the ozone/oxygen admixture entering the gas-fluid contacting device;
    g) an exit ozone concentration monitor that measures the concentration of an ozone/oxygen admixture exiting a gas-fluid contacting device; and
    h) a data acquisition device that cooperates with the gas-fluid contacting device, the ozone generator, the gas flow meter, the fluid pump, the variable pitch platform, the inlet ozone concentration monitor and the exit ozone concentration monitor, to determine: i. the elapsed-time during that the ozone/oxygen admixture interfaces with the fluid in the gas-fluid contacting device; ii. the amount of ozone in the ozone/oxygen admixture that is delivered to the gas-fluid contacting device; iii. the amount of ozone absorbed by the amount of fluid, within the gas-fluid contact device; and iv. the amount of ozone remaining in the ozone/oxygen admixture exiting the gas-fluid contact device; and wherein all ozone-contacting surfaces of said apparatus are constructed of material that is ozone-inert.

2. The apparatus of claim 1, wherein the elapsed-time ranges for a duration up to 120 hours.

3. The apparatus of claim 1, further comprising a plurality of gas-fluid contacting devices arranged in a series.

4. The apparatus of claim 1, wherein the gas-fluid contacting device contains a temperature sensor.

5. The apparatus of claim 1, wherein the gas-fluid contacting device contains a pressure sensor.

6. The apparatus of claim 1, wherein the ozone-inert construction materials include stainless steel, borosilicate, quartz, ceramic composites, PFA and PTFE.

7. An apparatus for delivering a measurable absorbed-dose of ozone to a fluid comprising:
    a gas-fluid contacting device including at least one variable pitch device, each variable device including a base having a flange extending around an open upper end thereof, a cover closing the open upper end of said base, and a plurality of bolts extending through the cover and flange to removably attach the cover to the base, the base and the cover together defining an enclosed chamber having an inlet end and an outlet end and that interfaces an ozone/oxygen admixture with a fluid, wherein a gas exit port and a fluid entrance port are disposed in the cover proximate said inlet end, a gas inlet port is disposed in the cover proximate said outlet end, and a fluid drain port is disposed in said base at proximate said outlet end;
    an ozone generator;
    a gas flow meter;
    a fluid pump;
    a variable pitch platform supporting the at least one variable pitch device, wherein said variable pitch platform includes a mechanism for adjusting the pitch of the at least one variable pitch device relative to a horizontal base of said platform, said variable pitch platform cooperating with the fluid pump to control the time during which the ozone/oxygen admixture interfaces with the fluid in the gas-fluid contacting device;

an inlet ozone concentration monitor;

an exit ozone concentration monitor; and a data acquisition device to control and measure the time during which and ozone/oxygen admixture interfaces with a measured amount of a fluid in the gas-fluid contacting device, and to compile and report data from the ozone generator, the gas flow meter, the fluid pump, the inlet ozone concentration monitor and the exit ozone concentration monitor, and to calculate an amount of ozone delivered to the gas-fluid contacting device and an amount of ozone absorbed by the measured amount of fluid;

wherein all ozone-contacting surfaces of said apparatus are constructed of material that is ozone-inert.

* * * * *